United States Patent [19]

Carr

[11] Patent Number: 5,120,878
[45] Date of Patent: Jun. 9, 1992

[54] PROCESS FOR THE PREPARATION OF SECONDARY MONOMETHYLALKYL AMINES

[75] Inventor: Eugene R. Carr, Chicago, Ill.

[73] Assignee: Akzo N.V., Arnhem, Netherlands

[21] Appl. No.: 647,910

[22] Filed: Jan. 30, 1991

[51] Int. Cl.$^5$ .......................................... C07C 209/00
[52] U.S. Cl. .................................................. 564/487
[58] Field of Search ............... 564/487, 489, 511, 499, 564/479, 486; 544/180

[56] References Cited

U.S. PATENT DOCUMENTS

| | | | |
|---|---|---|---|
| 2,657,237 | 10/1953 | Isham | 564/499 |
| 3,594,420 | 1/1971 | Gobron et al. | 564/487 |
| 4,138,437 | 2/1979 | Strauss et al. | 564/397 |

FOREIGN PATENT DOCUMENTS

| | | |
|---|---|---|
| 63-159362 | 7/1988 | Japan . |
| 1276740 | 6/1972 | United Kingdom . |
| 1305258 | 1/1973 | United Kingdom . |

OTHER PUBLICATIONS

Bequeme Darstellung von reinen N-Methylalkylaminen durch Zink/Salzsaure-Reduktion von 1,3,5-Tris-(alkyl)-hexahydro-1,3,5-triazinen, M. Shaik and H. Oelschlager, Arch. Pharm., 317, pp. 214-219, (1984), (with English language translation).

Polymeric Behavior of 1,3,5-tridodecyl- and 1,3,5-trioctadecylhexahydrosym-triazines, by C. W. Hoerr et al., J. Am. Chem. Soc., vol. 78, pp. 4667-4670, (1956).

*Primary Examiner*—Glennon H. Hollrah
*Assistant Examiner*—Shailendra Kumar
*Attorney, Agent, or Firm*—Louis A. Morris; David H. Vickrey

[57] ABSTRACT

A process for the preparation of secondary methylalkyl amines is disclosed, said process comprising reacting, at elevated temperature and pressure, a hexahydrotriazine compound in the liquid state with hydrogen in the presence of a catalyst material having at least one catalytically active metal, said hexahydrotriazine compound having the formula

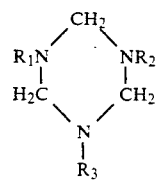

wherein $R_1$, $R_2$, and $R_3$ are, independently, straight or branched, saturated or unsaturated, linear or cyclic hydrocarbon groups or straight or branched, saturated or unsaturated, linear or cyclic hydrocarbon groups wherein one or more $CH_2$ groups are replaced by an oxygen atom or a tertiary amine group, provided that any unsaturated group is separated from nitrogen in the hexahydrotriazine ring by at least one carbon atom, any said oxygen atom is enclosed by two carbon groups and any said oxygen atoms and any said amine groups are separated from other oxygen atoms and other amine groups and from the nitrogen in the hexahydrotriazine ring by at least two carbon atoms.

8 Claims, No Drawings

PROCESS FOR THE PREPARATION OF SECONDARY MONOMETHYLALKYL AMINES

BACKGROUND OF THE INVENTION

The invention relates to a process for the preparation of secondary monomethylalkyl amines by reduction of a hexahydrotriazine compound in the presence of a metal component.

Such a process is known from U.S. Pat. No. 2,657,237 in which a process is given for the continuous preparation of dimethylamine by dissociation of trimethyl-trimethylene triamine into monomeric methylmethylene amine, and subsequent catalytic hydrogenation of the monomer into dimethylamine. The process taught is complicated in that it requires specific engineering and equipment to enable the continuous process to be carried out, and a mixture of hydrogen and the liquid trimethyltrimethylene triamine has to be vaporized in a separate preparatory step. Thus, the process is carried out by many sequential process steps, including the separate vaporization step, reaction of the components, separation of the reaction product and feeding the reaction product to a second reaction means. In the second reaction means gaseous reactants are to be passed through a catalyst, upon which dimethylamine is formed. Another drawback of such a process is that its use is uneconomical for the production of monomethyl amines having large alkyl groups, since vaporization of the precursors is rather complicated by their lower volatility.

"Bequeme Darstellung von reinen N-Methylalkylaminen durch Zink/Salzsaure-Reduktion von 1,3,5-Tris(alkyl)-hexahydro-1,3,5-triazinen", M. Al Schaik and H. Oelschläger, Arch. Pharm. 317, pp. 214-219 (1984) describes a process for preparation of n-methyl alkyl amines by zinc/hydrochloric acid reduction of trialkyl-hexahydrotriazines. The process is carried out at −5° C. using a drop-in procedure which is rather uneconomical. Further, the use of a chemical type of reduction is generally considered a major drawback. Together with the use of highly corrosive hydrochloric acid, the method described is expensive and difficult to practice on plant scale. Also the amine is obtained as its hydrochloric acid salt, from which it must be liberated with, for example, sodium hydroxide. Another drawback of this procedure is the large amount of zinc chloride waste produced and the rather low yield of the desired product obtained.

The Netherlands patent NL 7008733 relates to a method for the preparation of secondary or tertiary amines. In this patent specification, secondary or tertiary amines are prepared by reaction of a primary amine with formaldehyde in the presence of $H_2$, an alcohol and a catalyst. By this reaction, no hexahydrotriazine as used according to the present invention is formed, nor is a highly selective process for the production of secondary monomethylalkyl amines given.

SUMMARY OF THE INVENTION

The invention relates to a process for the preparation of secondary methylalkylamines, said process comprising reacting, at elevated temperature and pressure, a hexahydrotriazine compound in the liquid state with hydrogen in the presence of a catalyst material having at least one catalytically active metal.

The hexahydrotriazine compound has the formula

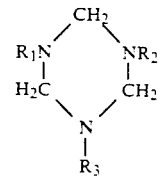

wherein $R_1$, $R_2$, and $R_3$ are, independently, straight or branched, saturated or unsaturated, linear or cyclic hydrocarbon groups or straight or branched, saturated or unsaturated, linear or cyclic hydrocarbon groups wherein one or more $CH_2$ groups are replaced by an oxygen atom or a tertiary amine group, provided that any unsaturated group is separated from nitrogen in the hexahydrotriazine ring by at least one carbon atom, any said oxygen atom is enclosed by two carbon groups and any said oxygen atoms and any said amine groups are separated from other oxygen atoms and other amine groups and from the nitrogen in the hexahydrotriazine ring by at least two carbon atoms.

Such a process provides favorable yield in case the contact time of the hydrogen, the hexahydrotriazine compound and the catalyst is at least 0.5 hour. In a preferred embodiment, the metal in the catalyst material contains copper. Such a process is preferably carried out at a temperature in the range of 170° C.-250° C. and a pressure in the range of 200-1500 psig for a period of at least one hour.

DETAILED DESCRIPTION OF THE INVENTION

The invention relates to a process for the preparation of secondary methylalkyl amines, said process comprising reacting, at elevated temperature and pressure, a hexahydrotriazine compound in the liquid state with hydrogen in the presence of a catalyst material having at least one catalytically active metal.

The hexahydrotriazine compound has the formula

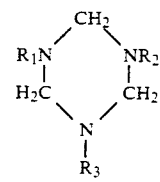

wherein $R_1$, $R_2$, and $R_3$ are, independently, straight or branched, saturated or unsaturated, linear or cyclic hydrocarbon groups or straight or branched, saturated or unsaturated, linear or cyclic hydrocarbon groups wherein one or more $CH$ groups are replaced by an oxygen atom or a tertiary amine group, provided that any unsaturated group is separated from nitrogen in the hexahydrotriazine ring by at least one carbon atom, any said oxygen atom is enclosed by two carbon groups and any said oxygen atoms and any said amine groups are separated from other oxygen atoms and other amine groups and from the nitrogen in the hexahydrotriazine ring by at least two carbon atoms.

By a hexahydrotriazine compound in the liquid state is meant that a hexahydrotriazine of the above formula is contacted with hydrogen and the catalyst without a separate preparatory vaporization step for the hexahydrotriazine.

It has been found that the process is satisfactorily carried out at an elevated temperature above 150° C. and an elevated pressure above 100 psig. Preferably, the process is carried out at a temperature between about 170° C. and 250° C. at a pressure about 200 to about 1500 psig. Contacting the hydrogen, the hexahydrotriazine compound and the catalyst for at least 0.5 hour, and preferably more than one hour, has provided favorable yields of secondary monomethylalkyl amines. In a highly economical embodiment of the present process, hexahydrotriazine compounds having large $R_1$, $R_2$ or $R_3$ groups are reacted at about 220° to about 230° C. and 400 psig for a period of between about 1 to 3 hours.

The hexahydrotriazine can of course be in solid or liquid state at room temperature. At reaction conditions, however, the hexahydrotriazine reacting in the process of the current invention will be substantially in the liquid state.

$R_1$, $R_2$, and $R_3$ of the hexahydrotriazine of the current invention can be, independently, straight or branched, saturated or unsaturated, linear or cyclic (e.g. alicyclic, aromatic, heterocyclic) hydrocarbon groups or straight or branched, saturated or unsaturated, linear or cyclic hydrocarbon groups wherein one or more $CH_2$ groups are replaced by an oxygen atom or a tertiary amine group, provided that any unsaturated group is separated from nitrogen in the hexahydrotriazine ring by at least one carbon atom, any said oxygen atom is enclosed by two carbon groups and any said oxygen atoms and any said amine groups are separated from other oxygen atoms and other amine groups and from said nitrogen in the hexahydrotri-azine ring by at least two carbon atoms.

The current process is particularly suitable for hexahydrotriazine compounds having at least one large $R_1$, $R_2$, or $R_3$ group. For the current process, a "large" group is one having about 4-40 carbon atoms. The process has shown to provide very useful products when $R_1$, $R_2$ and $R_3$, independently, have 8 to 30, preferably 12-22 carbon atoms. Examples of suitable groups for $R_1$, $R_2$, and/or $R_3$ are t-butyl, n-butyl, amyl, hexyl, benzyl, octyl, 2-ethylhexyl, 2-dodecyl-dodecyl, 1-heptadecyl-octadecyl, and the chains occurring in natural fatty compounds (e.g., coco, palm, and tallow compounds).

The process of the present invention results in highly selective production of the monomethylalkyl amine, in which the alkyl group can be any of the groups within the range discussed above. The product desired can be obtained in yields over 90%.

Products to be formed by the method of the present invention are, for example, N-methyl-t-butylamine, N-methyl benzyl amine, N-methyl dodecyl amine, N-methyl tallow amine, N-methyl-hydrogenated tallow amine, and N-methyl oleyl amine.

Highly favorable results are found if the catalyst material has copper as the catalytically active metal. Alternatively, another metal compound can be present with the copper as a promotor. For example, other metal oxides like potassium oxide, zinc oxide, magnesium oxide and/or barium oxide can be added to the catalyst. Other materials like chromite, alumina or silica can be applied with the metal component. Very good results were obtained by use of a catalyst having copper and chromium in the form of copper chromite, on which, additionally, barium can be present in minor amounts. Also a catalyst containing copper and zinc can be applied favorably.

The metal catalyst can be applied as such, but can also be distributed on and/or in a carrier material, such as, for example, silica and/or alumina, via methods such as impregnation or coprecipitation. Nickel-containing catalysts have been found not to be useful in the process of the present invention, since the use of such a catalytic material results in various by-products being formed.

It has been found that a very economical process is obtained if use is made of 0.5 wt. % copper catalyst, based on the weight of hexahydrotriazine present at initiation of the reaction. Favorably, use can be made of a copper chromite catalyst at a level of 0.5-0.75%, based on the weight of hexahydrotriazine. Additives can be used to influence the yield and speed of the reaction or to ease filtration after reaction.

The hexahydrotriazine applied in the process of the present invention can be prepared by any process known in the art. Such are commonly prepared by reaction of formaldehyde and a primary amine and removal of the water being formed. A useful method is described in, e.g., "Polymorphic Behavior of 1,3,5-tridodecyl- and 1,3,5-trioctadecylhexahydro-sym-triazines", by C. W. Hoerr et al., *J. Am. Chem. Soc.*, Vol. 78, pp. 4667-4670, (1956). By another method, the reaction is carried out by contacting the primary amine and formaldehyde at a temperature between 60°-85° C., and simultaneously stripping off the water being formed. By doing so, the product obtained is immediately cyclized to the triazine derivative. The reaction is completed by stripping off the volatiles. Another method especially useful for the formation of the hexahydrotriazine from lower amines is the reaction of an alkyl or alcyl amine with an aqueous formalin solution at a temperature in the range of 0° C.-5° C. The aqueous layer formed is separated. The desired hexahydrotriazine product can be dried by the addition of, e.g., calcium oxide.

Secondary monomethylalkyl amines produced by the process of the current invention are useful starting materials for further syntheses, such as, 1. alkoxylation,
2. alkoxylation and subsequent esterification and/or quaternization,
3. reaction with acrylonitrile and subsequent hydrogenation to the corresponding monomethyl diamine,
4. conversion with carbon disulfide to a dithocarbonate, and
5. conversion with carbon disulfide to a dithiocarbonate, followed by oxidation to a thiuram.

EXAMPLES 1-29

The following examples were carried out by addition of a hexahydrotriazine (2047 grams) in the liquid state and a catalyst in a 7.6 liter reaction vessel. The system was purged four times with 100 psig nitrogen and then vented to atmospheric pressure. The reactants were heated under nitrogen (vent open) to reaction temperature, unless indicated differently. Hydrogen gas was added and the pressure as indicated was maintained during the reaction. After the time indicated, the reaction vessel was cooled, and the product was removed. The weight yield was 98-100%.

Catalysts Used in the Examples i is a copper chromite-containing catalyst (42% CuO, 44% $Cr_2O_3$ and 8% of BaO) having a of surface area of 110 m2/g.

ii is a copper chromite-containing catalyst (51% CuO, 49% $Cr_2O_3$) having a surface area of 45 $m^2/g$.

iii is a copper chromite-containing catalyst (comprised of CuO and $Cr_2O_3$) known by the trade name Cu-1950P (available from Englehardt Corp.) having a surface area of 35 $m^2/g$.

iv is a copper chromite-containing catalyst (53% CuO, 47% $Cr_2O_3$) having a surface area of 34 $m^2/g$.

v is a copper chromite-containing catalyst (53% CuO, 47% $Cr_2O_3$) having a surface area of 88 $m^2/g$.

vi is a copper chromite-containing catalyst (45% CuO, 45% $Cr_2O_3$ and 8% BaO) having a surface area of 45 $m^2/g$.

vii is a copper chromite-containing catalyst (49% CuO, 47% $Cr_2O_3$ and 4% of $MnO_2$) having a surface area of 25 $m^2/g$.

viii is a copper containing catalyst (45% CuO, 45% ZnO) having a surface area of 12 $m^2/g$.

ix is a copper containing catalyst (91% CuO and 9% $Al_2O_3$) having a surface area of 100 $m^2/g$.

Hexahydrotriazine Reactant Used in the Examples

Reactant I is tallowalkyl hexahydrotriazine.
Reactant II is octadecyl hexahydrotriazine.
Reactant III is hydrogenated tallow hexahydrotriazine.

Products Obtained

Product A is tallow amine.
Product B is methyltallow amine.
Product C is dimethyltallow amine.
Product D is ditallow amine.
Product E is octadecylamine.
Product F is octadecylmethylamine.
Product G is dimethyloctadecylamine.
Product H is dioctadecylamine.
Product K is unreacted hexahydrotriazine.
Product P is hydrogenated tallow amine.
Product Q is hydrogenated methyl tallow amine.
Product R is hydrogenated dimethyl tallow amine.
Product S is hydrogenated ditallow amine.

EXAMPLES HAVING VARIATIONS FROM STANDARD REACTION CONDITIONS

Example 12

Hydrogen was added at 100° C., up to a pressure of 300 psig. The temperature was raised to 220° C., pressure 400 psig.

Example 13

As Example 12, but hydrogen was added at 130° C. and 300 psig.

Example 14

As Example 12, but hydrogen was added at 170° C. and 300 psig.

Example 21

This reaction employed a pressure increase (about 6 psig/min) and a gradient temperature increase (about 1°/min). The final temperature was 180° C., and the final pressure was 400 psig.

Example 22

In this example, tallow amine was produced by starting at 80° C. and 300 psig, and the reaction was carried out at 220° C. and 400 psig.

Example 23

As Examples 20, but the initial reaction conditions were 100° C. and 300 psig.

Example 30

1022 g (4 moles) of 1,3,5,-tri t-butyl hexahydro1,3,5 triazine, prepared from formaldehyde and t-butyl amine, and 10.2 g of a copper chromite catalyst, containing 53 wt. % CuO, and 47 wt.% $Cr_2O_3$ and having a surface area of 34 $m^2/g$, were charged to a 2.5 l stainless steel autoclave with a turbine stirrer and a hydrogen inlet pipe extending into the liquid. While stirring slowly the system was purged four times with 145 psig nitrogen, then four times with 145 psig hydrogen. The stirrer speed was increased to 1000 rpm and the reactor contents were heated to 140° C., while increasing the pressure to 220 psig. After two hours the temperature was increased gradually, over a period of two hours, to 200° C. while the pressure was increased to 850 psig. After three hours at 200° C., hydrogen consumption ceased. The reactor was cooled and emptied. The contents were filtrated and shown to contain 87 wt. % t-butyl methyl amine.

Comparative Examples

The process described for Examples 1-29 was used for Comparative Examples C1-C3 except the catalysts used in the Comparative Examples contained nickel compounds.

Catalysts Used x is a copper chromite-containing catalyst (46 wt. % CuO, 44 wt. % $Cr_2O_3$ and 10 wt. % NiO) having a surface area of 45 $m^2/g$.

xx is a nickel-containing catalyst, having a surface area of about 175 $m^2/g$, the catalyst comprised of about 60 wt. % nickel on a silica and alumina-containing carrier material.

xxx is a Raney nickel catalyst having a surface area of about 175 $m^2/g$.

From Comparative Examples C1-C3 it is seen that no selectivity was obtained for the catalysts containing nickel. While it is clear from Examples 1-30 that the use of copper at various reaction conditions provides favorable results.

TABLE 1

| Ex. | Cat. Type | React. | T (°C.) | P (psig) | Time (hours) | Cat. (wt %) | A | B | C | D | E | F | G | H | K |
|---|---|---|---|---|---|---|---|---|---|---|---|---|---|---|---|
| 1 | i | I | 220 | 400 | 1.5 | 1 | — | 85 | 15 | | | | | | |
| 2 | i | I | 220 | 200 | 1.8 | 1 | — | 72 | 7 | | | | | | 21 |
| 3 | i | I | 220 | 300 | 1.8 | 1 | — | 85 | 15 | | | | | | |
| 4 | i | I | 220 | 400 | 1.8 | 1 | — | 85 | 15 | | | | | | |
| 5 | i | I | 220 | 200 | 0.5 | | | | | | | | | | |
| | | | | 300 | 0.75 | 1 | — | 85 | 15 | | | | | | |
| 6 | ii | I | 220 | 400 | 1.5 | 1 | — | 80 | 20 | | | | | | |
| 7 | ii | I | 205 | 400 | 2 | 1 | — | 83 | 17 | | | | | | |

TABLE 1-continued

| Ex. | Cat. Type | React. | T (°C.) | P (psig) | Time (hours) | Cat. (wt %) | A | B | C | D | E | F | G | H | K |
|---|---|---|---|---|---|---|---|---|---|---|---|---|---|---|---|
| 8 | ii | I | 220 | 400 | 2 | 1 | — | 81 | 19 | | | | | | |
| 9 | ii | I | 260 | 400 | 2 | 1 | — | 68 | 32 | | | | | | |
| 10 | iii | I | 220 | 400 | 1.5 | 1 | — | 75 | 25 | | | | | | |
| 11 | iii | I | 220 | 400 | 3.5 | 1 | — | 76 | 24 | | | | | | |
| 12 | iv | II | see above | | 2 | 0.7 | | | | | 6.2 | 84.6 | 6.1 | 2.6 | 0.4 |
| 13 | iv | II | see above | | 2 | 0.7 | | | | | 5.0 | 84.9 | 6.7 | 2.6 | 0.7 |
| 14 | iv | II | see above | | 2 | 0.7 | | | | | 5.3 | 84.2 | 6.4 | 2.8 | 0.9 |
| 15A | iv | II | 220 | 400 | 0.5 | 0.7 | | | | | nil | nil | 4.4 | 1.8 | 93.1 |
| 15B | iv | II | 220 | 400 | 1 | 0.7 | | | | | 8.9 | 73.1 | 3.6 | 1.3 | 13.1 |
| 15C | iv | II | 220 | 400 | 1.5 | 0.7 | | | | | 6.8 | 80.4 | 6.2 | 2.1 | 4.6 |
| 15D | iv | II | 220 | 400 | 2 | 0.7 | | | | | 5.3 | 84.2 | 6.4 | 2.8 | 0.9 |
| 15E | iv | II | 220 | 400 | 2.5 | 0.7 | | | | | 5.4 | 83 | 6.8 | 4.3 | .02 |
| 16 | iv | II | 180 | 400 | 4 | 2 | | | | | 12.6 | 71.3 | 13.6 | 1.2 | 0.9 |
| 17 | iv | II | 220 | 400 | 1 | 2 | | | | | 9.5 | 78.2 | 7.8 | 2.5 | 0.8 |

TABLE 3

| Ex. | Cat. Type | T (°C.) | P (psig) | Time (hours) | Cat. (wt %) | Product obtained (% of total yield) | | | |
|---|---|---|---|---|---|---|---|---|---|
| | | | | | | A | B | C | D |
| C1 | x | 220 | 400 | 3.5 | 1 | — | 33 | 33 | 33 |
| C2 | xx | 120 | 200 | 4.5 | 1 | 32 | 18 | 35 | 15 |
| C3 | xxx | 140 | 200 | 4 | 1 | 19 | 28 | 27 | 26 |

TABLE 2

| Ex. | Cat. Type | React. | T (°C.) | P (psig) | Time (hours) | Cat. (wt %) | P | Q | R | S | E | F | G | H | K |
|---|---|---|---|---|---|---|---|---|---|---|---|---|---|---|---|
| 18 | iv | III | 230 | 400 | 2 | 0.7 | 7 | 82.1 | 5.4 | 5 | | | | | <0.1 |
| 19 | iv | III | 240 | 400 | 2 | 0.7 | 5.2 | 78.8 | 7.5 | 6.5 | | | | | nil |
| 20 | iv | III | 240 | 400 | 1 | 0.7 | 6.5 | 83.8 | 5.9 | 2.6 | | | | | 0.8 |
| 21 | iv | II | see above | | 5 | 0.7 | | | | | 4.1 | 82.4 | 6.4 | 1.7 | 3.9 |
| 22 | iv | III | see above | | 2 | 0.7 | 9.5 | 76.4 | 9.7 | 3.3 | | | | | 0.6 |
| 23 | iv | III | see above | | 2 | 0.7 | 6.2 | 84.6 | 6.1 | 2.6 | | | | | 0.4 |
| 24 | v | III | 220 | 400 | 2 | 0.7 | 3.0 | 89.0 | 4.5 | 3.5 | | | | | |
| 25 | v | III | 220 | 400 | 2.5 | 0.7 | 2.0 | 90.0 | 5.0 | 4.0 | | | | | |
| 26 | vi | III | 220 | 400 | 2 | 0.7 | 6.9 | 86.7 | 3.5 | trace | | | | | 2.9 |
| 27 | vii | III | 220 | 400 | 2 | 0.7 | 8.3 | 78.1 | 10.8 | 1.5 | | | | | 1.2 |
| 28 | viii | III | 220 | 400 | 2 | 0.7 | 9.0 | 76.0 | 4.8 | 3.4 | | | | | 6.2 |
| 29 | iv | III | 220 | 400 | 2 | 0.7 | 9.6 | 69.1 | 13.4 | 5.0 | | | | | 2.8 |

I claim:

1. A process for the preparation of secondary methylalkyl amines, said process comprising reacting, at elevated temperature and pressure, a hexahydrotriazine compound in the liquid state with hydrogen in the presence of a catalyst material comprising catalytically active copper substantially free of nickel, said hexahydrotriazine compound having the formula

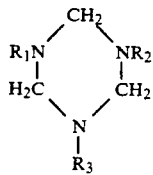

wherein $R_1$, $R_2$, and $R_3$ are independently, straight or branched, saturated or unsaturated, linear or cyclic hydrocarbon groups or straight or branched, saturated or unsaturated, linear or cyclic hydrocarbon groups wherein one or more $CH_2$ groups are replaced by an oxygen atom or a tertiary amine group, provided that any unsaturated group is separated from nitrogen in the hexahydrotriazine ring by at least one carbon atom, any said oxygen atom is enclosed by two carbon groups and any said oxygen atoms and any said amine groups are separated from other oxygen atoms and other amine groups and from the nitrogen in the hexahydrotriazine ring by at least two carbon atoms.

2. A process according to claim 1 wherein $R_1$, $R_2$ and $R_3$ each have at least 4 carbon atoms.

3. A process according to claim 1 wherein the contact time of the alkyl hexahydrotriazine and the hydrogen is at least 0.5 hour.

4. A process according to claim 1 wherein said catalyst material is further comprised of copper chromite.

5. A process according to claim 4 in which the catalyst is present in an amount of at least 0.5% by weight, calculated as the weight of copper chromite on the weight of hexahydrotriazine.

6. A process according to claim 1 in which the reaction is carried out at a temperature in the range of about 170° to about 250° C., a pressure in the range of about 200 to about 1500 psig for a period of at least one hour.

7. A process according claim 3 in which the process is carried out at a temperature in the range of 200° C.–250° C. and a pressure in the range of 350 to 1000 psig for a period of at least 1 hour.

8. A process according to claim 2 wherein the hexahydrotriazine is selected from the group consisting of hexahydrotriazines wherein at least one of $R_1$, $R_2$, and $R_3$ is a straight or branched alkyl group having 12 to 22 carbon atoms.

* * * * *